US010142550B2

(12) United States Patent
Gladnick

(10) Patent No.: US 10,142,550 B2
(45) Date of Patent: Nov. 27, 2018

(54) EXTENDING A FOCUS SEARCH RANGE IN AN IMAGING SYSTEM INCLUDING A HIGH SPEED VARIABLE FOCAL LENGTH LENS

(71) Applicant: Mitutoyo Corporation, Kanagawa-ken (JP)

(72) Inventor: Paul Gerard Gladnick, Seattle, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 220 days.

(21) Appl. No.: 15/352,472

(22) Filed: Nov. 15, 2016

(65) Prior Publication Data

US 2018/0139390 A1    May 17, 2018

(51) Int. Cl.
  *G03B 13/32* (2006.01)
  *H04N 5/232* (2006.01)
  (Continued)

(52) U.S. Cl.
  CPC ..... *H04N 5/23296* (2013.01); *G01N 21/8806* (2013.01); *G02B 3/0081* (2013.01);
  (Continued)

(58) Field of Classification Search
  CPC .. C12Q 1/6886; C12Q 1/68; C12Q 2600/158; C12Q 2600/106; G01N 33/57415;
  (Continued)

(56) References Cited

U.S. PATENT DOCUMENTS

| 4,905,032 A * | 2/1990 | Ishida .................. G02B 7/346 396/104 |
| 5,144,357 A * | 9/1992 | Ishida .................. G02B 7/346 250/201.2 |

(Continued)

OTHER PUBLICATIONS

Gladnick, "Adaptable Operating Frequency of a Variable Focal Length Lens in an Adjustable Magnification Optical System," U.S. Appl. No. 14/795,409, filed Jul. 9, 2015, 36 pages.

(Continued)

*Primary Examiner* — Sathyanaraya V Perungavoor
*Assistant Examiner* — Howard D Brown, Jr.
(74) *Attorney, Agent, or Firm* — Seed IP Law Group LLP

(57) ABSTRACT

A method for controlling an imaging system comprising a variable focal length (VFL) lens having first and second operating resonant frequencies, a lens controller, and a camera is disclosed. The first frequency provides a larger optical power variation and large focus range, at the expense of aberration in the imaging system. The second frequency provides a smaller optical power variation and small focus range, but provides low aberration in the imaging system. The method comprises: providing an extended focus range demand to the lens controller and, in response, configuring the lens controller to operate the VFL lens at the first resonant frequency (e.g., to provide a large autofocus search range). The method further comprises: providing an accurate image demand signal to the lens controller and, in response, configuring the lens controller to operate the VFL lens at the second resonant frequency (e.g., to provide low aberration images).

18 Claims, 5 Drawing Sheets

(51) Int. Cl.
  *G02B 3/00*   (2006.01)
  *G02B 27/00*  (2006.01)
  *G06T 7/00*   (2017.01)
  *G01N 21/88*  (2006.01)
  *H04N 5/225*  (2006.01)

(52) U.S. Cl.
  CPC ........ *G02B 27/0068* (2013.01); *G06T 7/0004* (2013.01); *G06T 7/0042* (2013.01); *H04N 5/23212* (2013.01); *H04N 5/23216* (2013.01); *G01N 2201/12* (2013.01); *G06T 2207/30164* (2013.01); *H04N 5/2256* (2013.01); *H04N 5/23293* (2013.01)

(58) Field of Classification Search
  CPC ......... G01N 33/57484; G01N 2800/52; C12M 1/34; A61K 31/704
  See application file for complete search history.

(56) References Cited

U.S. PATENT DOCUMENTS

| | | | |
|---|---|---|---|
| 6,542,180 B1 | 4/2003 | Wasserman et al. | |
| 7,324,682 B2 | 1/2008 | Wasserman | |
| 7,454,053 B2 | 11/2008 | Bryll et al. | |
| 8,111,905 B2 | 2/2012 | Campbell | |
| 8,111,938 B2 | 2/2012 | Bryll et al. | |
| 9,060,117 B2 | 6/2015 | Bryll et al. | |
| 9,143,674 B2 | 9/2015 | Gladnick | |
| 2008/0049137 A1* | 2/2008 | Endo | H04N 5/23212 348/333.13 |
| 2009/0202235 A1* | 8/2009 | Li | H04N 5/23212 396/125 |
| 2012/0026386 A1* | 2/2012 | Tomita | G02B 7/36 348/345 |
| 2014/0368726 A1 | 12/2014 | Gladnick | |
| 2018/0139390 A1* | 5/2018 | Gladnick | H04N 5/23296 |

OTHER PUBLICATIONS

Mermillod-Blondin et al., "High-speed varifocal imaging with a tunable acoustic gradient index of refraction lens," *Optics Letters* 33(18):2146-2148, 2008.

Mitutoyo, "QVPAK 3D CNC Vision Measuring machine," Operation Guide Version 2.0, Sep. 1996, 86 pages.

Mitutoyo, "QVPAK 3D CNC Vision Measuring Machine," User's Guide, Version 7, Jan. 2003, 329 pages.

\* cited by examiner

EXTENDING A FOCUS SEARCH RANGE IN AN IMAGING SYSTEM INCLUDING A HIGH SPEED VARIABLE FOCAL LENGTH LENS

BACKGROUND

Technical Field

This disclosure relates to precision metrology using a machine vision inspection system, and more particularly to automatically determining an approximate adjustment distance in order to bring the workpiece to be inspected into a desirable focus range in a machine vision inspection system.

Description of the Related Art

Precision non-contact metrology systems such as precision machine vision inspection systems (or "vision systems" for short) may be utilized to obtain precise dimensional measurements of objects and to inspect various other object characteristics, and may include a computer, a camera and optical system, and a precision stage that moves to allow workpiece traversal and inspection. One exemplary prior art system, characterized as a general-purpose "off-line" precision vision system, is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, and the QVPAK 3D CNC Vision Measuring Machine Operation Guide, published September 1996, each of which is hereby incorporated by reference in its entirety. This type of system uses a microscope-type optical system and moves the stage so as to provide inspection images of either small or relatively large workpieces.

General-purpose precision machine vision inspection systems are generally programmable to provide automated video inspection. Such systems typically include GUI features and predefined image analysis "video tools" such that operation and programming can be performed by "non-expert" operators. For example, U.S. Pat. No. 6,542,180, which is incorporated herein by reference in its entirety, teaches a vision system that uses automated video inspection including the use of various video tools.

Multi-lens variable focal length (VFL) optical systems may be utilized in a precision machine vision inspection system, for example as disclosed in U.S. Pat. No. 9,143,674, which is hereby incorporated herein by reference in its entirety. In various applications utilizing such a VFL optical system, the clear aperture of a VFL lens included in the multi-lens optical system is generally sized such that it does not contribute to excessive vignetting or aberrations, in the precision inspection images that are required from the optical system. However, for some VFL lenses (e.g., such as tunable acoustic gradient (TAG) lenses in particular) the clear aperture (e.g., a distortion free central aperture dimension) depends on the VFL modulation frequency of the VFL lens and the modulation amplitude, and the VFL lens operating frequency (or modulation frequency) and modulation amplitude has been determined and/or limited based at least partly on this design consideration. For some VFL lenses (e.g., such as TAG lenses in particular) the constrained operating frequency outlined above concomitantly determines and/or limits other frequency-dependent characteristics of the VFL lens (e.g., a TAG lens), such as the variation in focus range or optical power that it is able to provide throughout a periodic cycle of the VFL modulation frequency. Related discussion and teachings may be found, for example, in commonly assigned copending U.S. patent application Ser. No. 14/795,409, to Gladnick, which is hereby incorporated herein by reference in its entirety.

As is well known to users of precision machine vision inspection systems, a workpiece surface may come to be positioned outside of a focus range of their optical system, even when it includes a VFL lens. "Searching" and/or attempting to autofocus on such a workpiece surface based on mechanical adjustment of the spacing between the workpiece and the optical system may be slow and/or risky due to the potential for crashing a lens into the workpiece during the "searching" motion. There is a need for high speed operations for searching and/or attempting to autofocus on such a workpiece surface over an extended search range, while at the same time eliminating the risk of crashing a lens into the workpiece during a searching motion.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method for controlling an imaging system is disclosed. The imaging system comprises a high speed variable focal length (VFL) lens having a first operating resonant frequency that provides a periodically modulated first optical power variation having a relatively larger amplitude, and having a second operating resonant frequency that provides a periodically modulated second optical power variation having a relatively smaller amplitude and that provides relatively low aberration in the imaging system; a lens controller; and a camera configured to provide images for the imaging system. The method comprises: providing an extended focus range demand signal to the lens controller; in response to the extended focus range demand signal, configuring the lens controller to operate the VFL lens at the first operating resonant frequency to provide the first optical power variation, and thereby provide a first relatively larger focus range for the imaging system; providing an accurate image demand signal to the lens controller; and in response to the accurate image demand signal, configuring the lens controller to operate the VFL lens at the second operating resonant frequency to provide the second optical power variation, and thereby provide a second relatively smaller focus range and low aberration images for the imaging system.

Operating at the second operating resonant frequency may be characterized as operating the VFL lens in a "normal" imaging mode, wherein the VFL is operated to provide desirable optical characteristics (e.g., in terms of clear aperture, low aberrations, etc.) that are furthermore well matched to the other optical components in the imaging system. In contrast, when operating at the first operating resonant frequency, the primary or only purpose may be to provide the first relatively larger focus range (e.g., to enable a large autofocus search range.) In various implementations, this may be characterized as operating the VFL lens in an abnormal imaging mode, wherein the emphasis on obtaining a larger optical power variation and focus range requires the acceptance of certain undesirable optical characteristics (e.g., in terms of clear aperture size, low aberrations, etc.) that are furthermore poorly matched to the other optical components in the imaging system. As a result, in some implementations, in this mode the imaging system may only provide relatively aberrated or blurry images that are not suited for precision metrology inspection operations. Nevertheless, such images have significant utility according to principles disclosed herein. For example, they are usable for performing autofocus search operations over an extended range, without the need for mechanically reconfiguring and moving an imaging system in order to do so.

DETAILED DESCRIPTION

Figure 1:
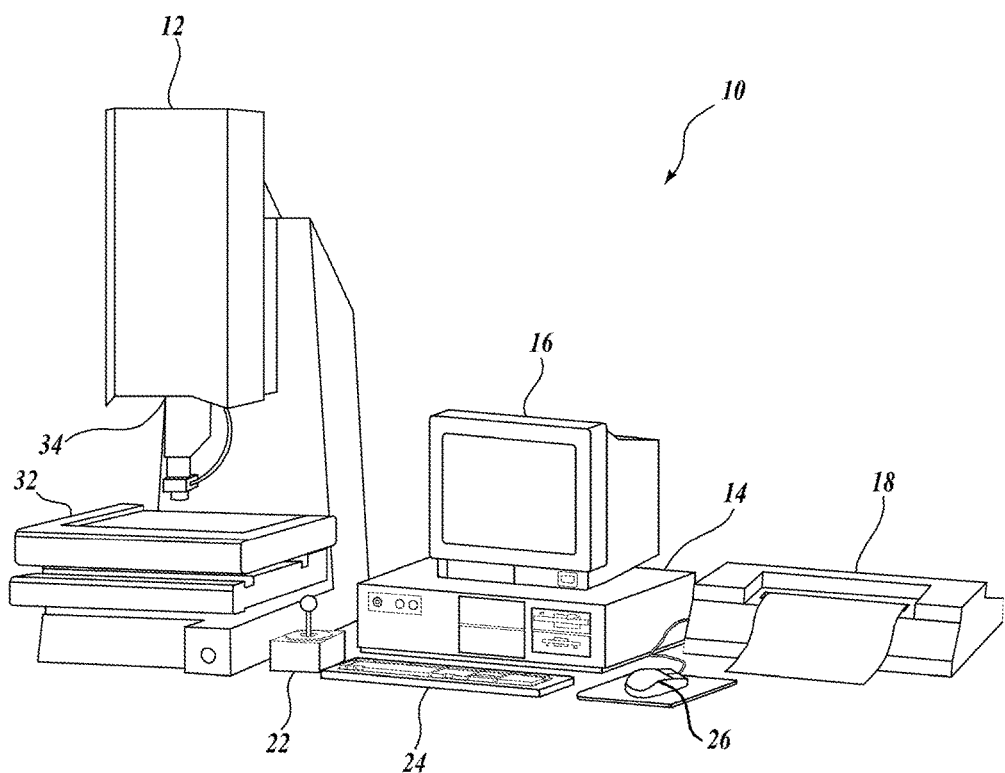
FIG. 1 is a diagram showing various typical components of a general-purpose precision machine vision inspection system.

FIG. 1 is a block diagram of one exemplary machine vision inspection system 10 usable in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10. It will be appreciated that in various implementations, a touchscreen tablet or the like may be substituted for and/or redundantly provide the functions of any or all of the computer system 14, the display 16, the joystick 22, the keyboard 24, and the mouse 26.

Those skilled in the art will appreciate that the controlling computer system 14 may generally consist of any computing system or device. Suitable computing systems or devices may include personal computers, server computers, minicomputers, mainframe computers, distributed computing environments that include any of the foregoing, and the like. Such computing systems or devices may include one or more processors that execute software to perform the functions described herein. Processors include programmable general-purpose or special-purpose microprocessors, programmable controllers, application-specific integrated circuits (ASICs), programmable logic devices (PLDs), or the like, or a combination of such devices. Software may be stored in memory, such as random-access memory (RAM), read-only memory (ROM), flash memory, or the like, or a combination of such components. Software may also be stored in one or more storage devices, such as optical-based disks, flash memory devices, or any other type of non-volatile storage medium for storing data. Software may include one or more program modules that include routines, programs, objects, components, data structures, and so on that perform particular tasks or implement particular abstract data types. In distributed computing environments, the functionality of the program modules may be combined or distributed across multiple computing systems or devices and accessed via service calls, either in a wired or wireless configuration.

The vision measuring machine 12 includes a moveable workpiece stage 32 and an optical imaging system 34 that may include a zoom lens or interchangeable lenses. The zoom lens or interchangeable lenses generally provide various magnifications for the images provided by the optical imaging system 34. The machine vision inspection system 10 is also described in commonly assigned U.S. Pat. Nos. 7,454,053; 7,324,682; 8,111,905; and 8,111,938, each of which is hereby incorporated herein by reference in its entirety.

Figure 2:
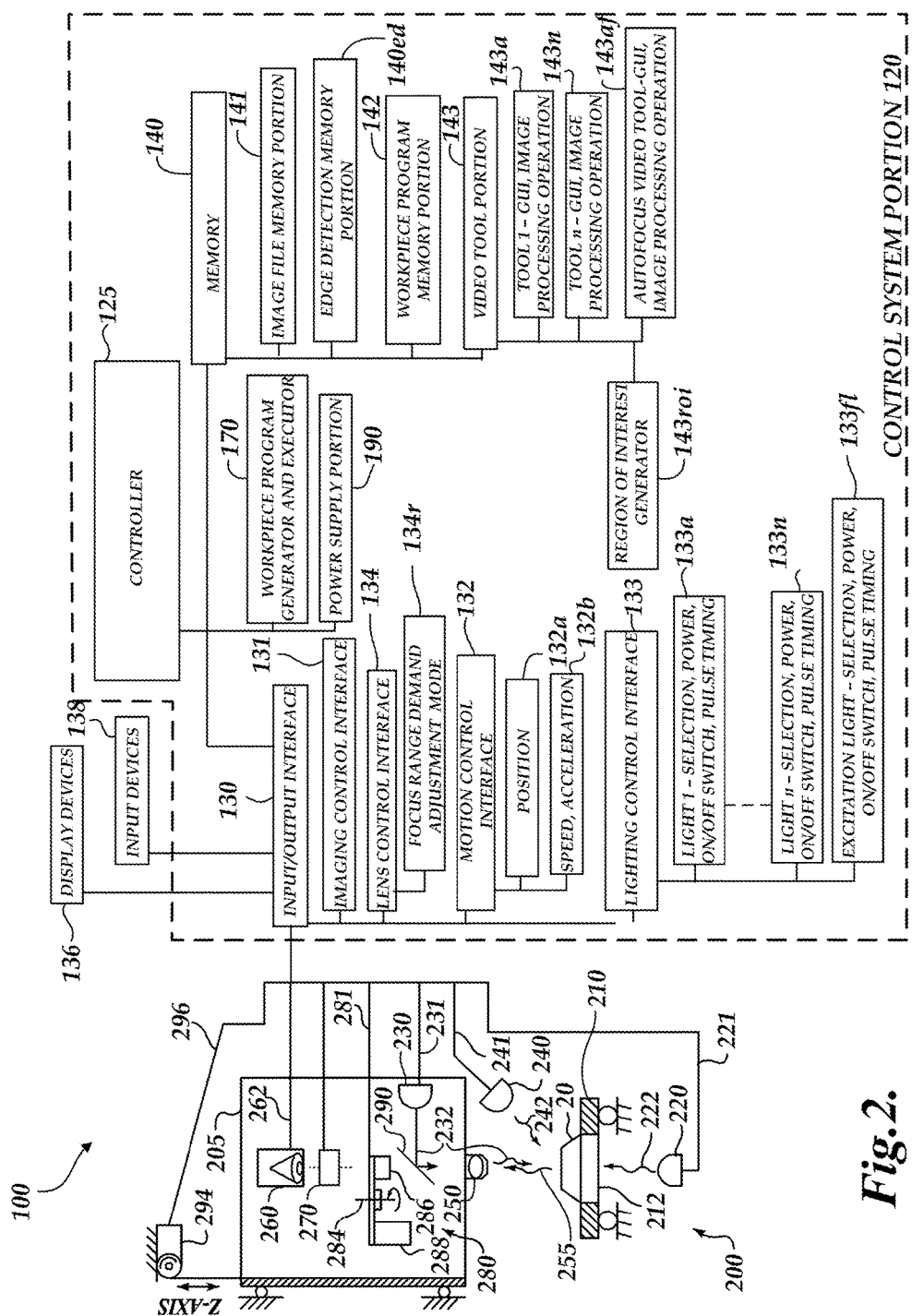
FIG. 2 is a block diagram of a control system portion and a vision components portion of a machine vision inspection system similar to that of FIG. 1 and including features disclosed herein.

FIG. 2 is a block diagram of a control system portion 120 and a vision components portion 200 of a machine vision inspection system 100 similar to the machine vision inspection system of FIG. 1, and including features as described herein. As will be described in more detail below, the control system portion 120 is utilized to control the vision components portion 200. The vision components portion 200 includes an optical assembly portion 205, light sources 220, 230, and 240, and a workpiece stage 210 having a central transparent portion 212. The workpiece stage 210 is controllably movable along x- and y-axes that lie in a plane that is generally parallel to the surface of the stage where a workpiece 20 may be positioned.

The optical assembly portion 205 includes a camera system 260, an interchangeable objective lens 250, a variable focal length (VFL) lens 270, and may include a turret lens assembly 280 having lenses 286 and 288. Alternatively to the turret lens assembly, a fixed or manually interchangeable magnification-altering lens, or a zoom lens configuration, or the like, may be included. In various implementations, the various lenses may be included as part of a variable magnification lens portion of the optical assembly portion 205. In various implementations, the interchangeable objective lens 250 may be selected from a set of fixed magnification objective lenses that are included as part of the variable magnification lens portion (e.g., a set of objective lenses corresponding to magnifications such as 0.5×, 1×, 2× or 2.5×, 5×, 10×, 20× or 25×, 50×, 100×, etc.).

The optical assembly portion 205 is controllably movable along a z-axis that is generally orthogonal to the x- and y-axes by using a controllable motor 294 that drives an actuator to move the optical assembly portion 205 along the z-axis to change the focus of the image of the workpiece 20. The controllable motor 294 is connected to an input/output interface 130 via a signal line 296. As will be described in more detail below, the VFL lens 270 may also be operated to periodically modulate a focus position. A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20.

One or more of a stage light 220, a coaxial light 230, and a surface light 240 (e.g., a ring light) may emit source light 222, 232, and/or 242, respectively, to illuminate the workpiece or workpieces 20. The coaxial light 230 may emit light 232 along a path including a mirror 290. The source light is reflected or transmitted as workpiece light 255, and the workpiece light used for imaging passes through the interchangeable objective lens 250, the turret lens assembly 280 and the VFL lens 270 and is gathered by the camera system 260. The image of the workpiece(s) 20, captured by the camera system 260, is output on a signal line 262 to the control system portion 120. The light sources 220, 230, and 240 may be connected to the control system portion 120 through signal lines or busses 221, 231, and 241, respectively. The control system portion 120 may rotate the turret lens assembly 280 along axis 284 to select a turret lens through a signal line or bus 281 to alter an image magnification.

As shown in FIG. 2, in various exemplary implementations, the control system portion 120 includes a controller 125, the input/output interface 130, a memory 140, a workpiece program generator and executor 170, and a power supply portion 190. Each of these components, as well as the additional components described below, may be interconnected by one or more data/control busses and/or application programming interfaces, or by direct connections between the various elements. The input/output interface 130 includes an imaging control interface 131, a motion control interface 132, a lighting control interface 133, and a lens control interface 134. The lens control interface 134 may include a lens controller including a lens focus operating circuit and/or routine, or the like. The lens control interface 134 may include focus range demand adjustment mode portion, circuit, or routine 134r, which is generally operable according to principles disclosed herein, and/or as described in greater detail below with reference to the focus range demand adjustment portion, circuit, or routine 334r shown in FIG. 3. In some embodiments the two may be merged and/or indistinguishable. The motion control interface 132 may include a position control element 132a, and a speed/acceleration control element 132b, although such elements may be merged and/or indistinguishable. The lighting control interface 133 may include lighting control elements 133a, 133n, and 133fl that control, for example, the selection, power, on/off switch, and strobe pulse timing, if applicable, for the various corresponding light sources of the machine vision inspection system 100.

The memory 140 may include an image file memory portion 141, an edge-detection memory portion 140ed, a workpiece program memory portion 142 that may include one or more part programs, or the like, and a video tool portion 143. The video tool portion 143 includes video tool portion 143a and other video tool portions (e.g., 143n) that determine the GUI, image-processing operation, etc., for each of the corresponding video tools, and a region of interest (ROI) generator 143roi that supports automatic, semi-automatic, and/or manual operations that define various ROIs that are operable in various video tools included in the video tool portion 143. The video tool portion also includes an autofocus video tool 143af that determines the GUI, image-processing operation, etc., for focus height measurement operations. In various implementations, the autofocus video tool 143af may additionally include a high-speed focus height tool that may be utilized to measure focus heights with high speed using hardware described in FIG. 3, as described in more detail in copending and commonly assigned U.S. Patent Publication No. 2014/0368726, which is hereby incorporated herein by reference in its entirety. In various implementations, the high-speed focus height tool may be a special mode of the autofocus video tool 143af that may otherwise operate according to conventional methods for autofocus video tools, or the operations of the autofocus video tool 143af may only include those of the high-speed focus height tool.

In the context of this disclosure, and as is known by one of ordinary skill in the art, the term "video tool" generally refers to a relatively complex set of automatic or programmed operations that a machine vision user can implement through a relatively simple user interface (e.g., a graphical user interface, editable parameter windows, menus, and the like), without creating the step-by-step sequence of operations included in the video tool or resorting to a generalized text-based programming language, or the like. For example, a video tool may include a complex pre-programmed set of image-processing operations and computations that are applied and customized in a particular instance by adjusting a few variables or parameters that govern the operations and computations. In addition to the underlying operations and computations, the video tool comprises the user interface that allows the user to adjust those parameters for a particular instance of the video tool. For example, many machine vision video tools allow a user to configure a graphical region of interest (ROI) indicator through simple "handle dragging" operations using a mouse, in order to define the location parameters of a subset of an image that is to be analyzed by the image-processing operations of a particular instance of a video tool. It should be noted that the visible user interface features are sometimes referred to as the video tool, with the underlying operations being included implicitly.

The signal lines or busses 221, 231, and 241 of the stage light 220, the coaxial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) may also be connected to the input/output interface 130. The display devices 136 and input devices 138 may be used to display a user interface that may include various graphical user interface (GUI) features that are usable to perform inspection operations, and/or to create and/or modify part programs, to view the images captured by the camera system 260, and/or to directly control the vision system components portion 200. The display devices 136 may display user interface features (e.g., as associated with the autofocus video tool 143af, etc.).

In various exemplary implementations, when a user utilizes the machine vision inspection system 100 to create a part program for the workpiece 20, the user generates part program instructions by operating the machine vision inspection system 100 in a learn mode to provide a desired image-acquisition training sequence. For example, a training sequence may comprise positioning a particular workpiece feature of a representative workpiece in the field of view (FOV), setting light levels, focusing or autofocusing, acquiring an image, and providing an inspection training sequence applied to the image (e.g., using an instance of one of the video tools on that workpiece feature). The learn mode operates such that the sequence(s) are captured or recorded and converted to corresponding part program instructions. These instructions, when the part program is executed, will cause the machine vision inspection system to reproduce the trained image acquisition and cause inspection operations to automatically inspect that particular workpiece feature (that is the corresponding feature in the corresponding location) on a run mode workpiece, or workpieces, which matches the representative workpiece used when creating the part program.

Figure 3:
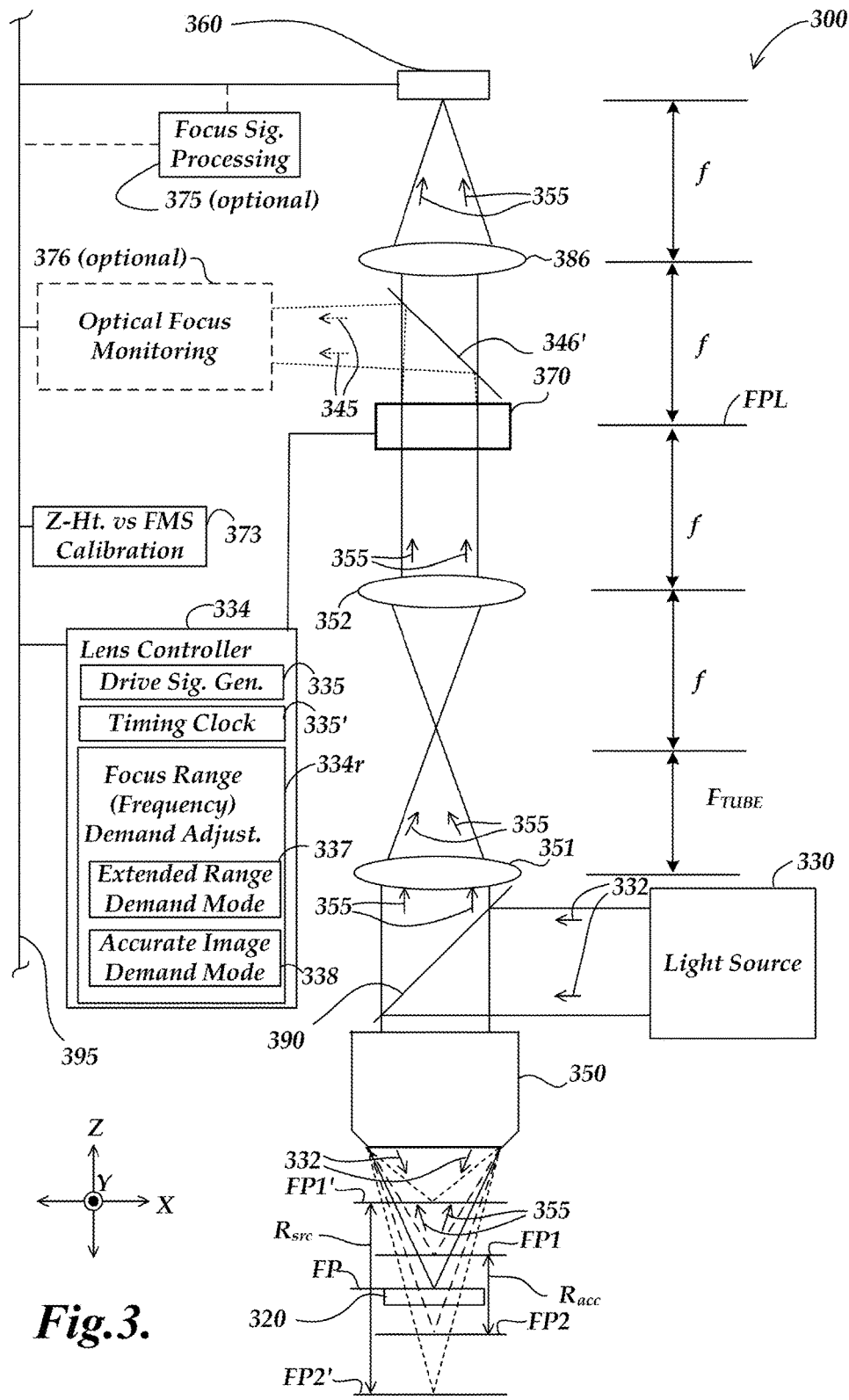
FIG. 3 is a schematic diagram of an imaging system that may be adapted to a precision non-contact metrology system such as a machine vision inspection system and operated according to the principles disclosed herein.

FIG. 3 is a schematic diagram of a VFL lens system 300 (also referred to as imaging system 300) that may be adapted to a vision system and operated according to the principles disclosed herein. It will be appreciated that certain numbered components 3XX of FIG. 3 may correspond to and/or have similar operations as similarly numbered components 2XX of FIG. 2, except as otherwise described below. As shown in FIG. 3, the VFL lens system 300 includes a light source 330, an objective lens 350, a tube lens 351, a relay lens 352, a VFL lens 370, a relay lens 386, a lens controller 334, a camera/detector 360, an optical focus monitoring portion 376, and an optional focus monitoring signal (FMS) calibration portion 373. In various implementations, the various components may be interconnected by direct connections or one or more data/control busses (e.g., a system signal and control bus 395) and/or application programming interfaces.

In operation, in the implementation shown in FIG. 3, the light source 330 may be a "coaxial" or other light source configured to emit the source light 332 (e.g., with strobed or continuous illumination) along a path including a partial mirror 390 and through the objective lens 350 to a surface of a workpiece 320, wherein the objective lens 350 receives the workpiece light 355 that is focused at a focus position FP proximate to the workpiece 320, and outputs the workpiece light 355 to the tube lens 351. The tube lens 351 receives the workpiece light 355 and outputs it to the relay lens 352. In other implementations, analogous light sources may illuminate the field of view in a non-coaxial manner, for example a ring light source may illuminate the field of view. In various implementations, the objective lens 350 may be an interchangeable objective lens and the tube lens 351 may be included as part of a turret lens assembly (e.g., similar to the interchangeable objective lens 250 and the turret lens assembly 280 of FIG. 2). In various implementations, any of the other lenses referenced herein may be formed from or operate in conjunction with individual lenses, compound lenses, etc.

The relay lens 352 receives the workpiece light 355 and outputs it to the VFL lens 370. The VFL lens 370 receives the workpiece light 355 and outputs it to the relay lens 386. The relay lens 386 receives the workpiece light 355 and outputs it to the camera/detector 360. In various implementations, the camera/detector 360 may capture an image of the workpiece 320 during an image exposure period, and may provide the image data to a control system portion.

In the example of FIG. 3, the relay lenses 352 and 386 and the VFL lens 370 are designated as being included in a 4f optical configuration, while the relay lens 352 and the tube lens 351 are designated as being included in a Keplerian telescope configuration, and the tube lens 351 and the objective lens 350 are designated as being included in a microscope configuration. All of the illustrated configurations will be understood to be exemplary only, and not limiting with respect to the present disclosure. In various implementations, the illustrated 4f optical configuration permits placing the VFL lens 370 (e.g., which may be a low numerical aperture (NA) device, such as a TAG lens), at the Fourier plane FPL of the objective lens 350. This configuration may maintain the telecentricity at the workpiece 320 and may minimize scale change and image distortion (e.g., including providing constant magnification for each Z-height of the workpiece 320 and/or focus position FP). The Keplerian telescope configuration (e.g., including the tube lens 351 and the relay lens 352) may be included between the microscope configuration and the 4f optical configuration, and may be configured to provide a desired size of the projection of the objective lens clear aperture at the location of the VFL lens, so as to minimize image aberrations, etc.

In various implementations, the optional focus signal processing portion 375 may input data from the camera/detector 360 and may provide data or signals that are utilized to determine when an imaged surface region (e.g., of the workpiece 320) is at a focus position. For example, in an implementation where the camera/detector 360 includes a camera, one or more images acquired by the camera (e.g., an image stack), may be analyzed using a known "maximum contrast" analysis to determine when an imaged surface region of the workpiece 320 is at a focus position. Exemplary techniques for such an analysis are taught in U.S. Pat. Nos. 6,542,180 and 9,060,117, each of which is commonly assigned and hereby incorporated herein by reference in its entirety. In another implementation, the optical focus monitoring portion 376 may provide a focus monitoring signal (e.g., a signal from a photodetector) derived for image light 345 that passes through the VFL lens 370 and is deflected from a beamsplitter 346' to the optical focus monitoring portion 376. In one embodiment, the optical focus monitoring portion 376 may comprise a confocal optical detector configuration. However, more generally any other suitable known focus detection configuration may be used. In some implementations, a focus monitoring signal may be determined which is directly indicative of the periodic focus modulation, approximately in real time.

In any case, the focus signal processing portion 375 or the optical focus monitoring portion 376 may input image light during the periodic modulation of the optical power of the VFL lens 370 and output a corresponding signal to the Z-height versus focus monitoring signal calibration portion 373 that indicates when the focus position FP of the imaging system 300 corresponds to an imaged surface of the workpiece 320. In various implementations, the Z-height versus focus monitoring signal calibration portion 373 may provide a first Z-height versus focus monitoring signal value characterization that relates respective Z-heights to respective focus monitoring signal values. Generally speaking, the Z-height versus focus monitoring signal calibration portion 373 comprises recorded calibration data. As such, its representation in FIG. 3 as a separate element is only schematic, and not limiting. The associated recorded calibration data could be merged with and/or indistinguishable from the lens controller 334, or the optical focus monitoring portion 376, or a host computer system connected to the system signal and control bus 395, in various implementations.

In various implementations, a vision system may comprise a control system (e.g., the control system portion 120 of FIG. 2) that is configurable to operate in conjunction with a lens controller 334 or to otherwise control the VFL lens 370 to periodically modulate a focus position of the VFL lens system 300. In some implementations, the VFL lens 370 may rapidly adjust or modulate the focus position periodically. In various implementations, the lens controller 334 may operate to drive the VFL lens 370 (e.g., a TAG lens) at a resonant frequency in order to periodically modulate the VFL lens optical power over the range of optical powers at the operating frequency. In various implementations, the periodically modulated VFL lens optical power may define a periodic focus modulation of the imaging system 300. In various implementations, the adjustment of the control of the VFL lens 370 may include adjusting at least one of the amplitude, frequency, or phase of the periodic modulation of the VFL lens 370. In various implementations a periodic modulation of 300 Hz, or 3 kHz, or 70 kHz, or 250 kHz, or the like, may be used. In implementations where slower periodic focus position adjustments are used, the VFL lens 370 may comprise a controllable fluid lens, or the like.

In various implementations, the VFL lens 370 may be a tunable acoustic gradient index of refraction ("TAG") lens. A tunable acoustic gradient index of refraction lens is a high-speed VFL lens that uses sound waves in a fluid medium to modulate a focus position, and may periodically sweep a range of focal lengths at a frequency of several hundred kHz. Such a lens may be understood by the teachings of the article, "High-speed varifocal imaging with a tunable acoustic gradient index of refraction lens" (Optics Letters, Vol. 33, No. 18, Sep. 15, 2008), which is hereby incorporated herein by reference in its entirety. Tunable acoustic gradient index lenses and related controllable signal generators are available, for example, from TAG Optics, Inc., of Princeton, N.J. The Model TL2.B.xxx series lenses, for example, are capable of modulation up to approximately 600 kHz.

In one implementation, the lens controller 334 may be a commercial controllable signal generator. In some implementations, the lens controller 334 may be configured or controlled by a user and/or an operating program (e.g., through the lens control interface 134, as outlined previously with respect to FIG. 2), or the two may be merged and/or indistinguishable in some implementations. In various implementations, the lens controller 334 may include a drive signal generator portion 335. The drive signal generator portion 335 may operate (e.g., in conjunction with a timing clock 335') to provide a periodic drive signal to a high speed VFL such as a TAG lens. In various implementations, the periodic signal may have the same operating frequency as the periodically modulated VFL lens optical power, and in a prior art TAG lens the approximate focus height or Z-height of a TAG lens has been determined based on a concurrent state of the drive signal.

In various implementations, the lens controller 334 may include focus range demand adjustment portion, circuit, or routine 334r, which is operable according to principles disclosed herein. In some embodiments the two may be merged and/or indistinguishable. In either case, the focus range demand adjustment portion 334r may be configured to alter the operating frequency that the lens controller 334 uses to drive the VFL lens 370, in response to a focus range demand signal that is input to the focus range demand adjustment portion 334r. In one embodiment, the focus range demand adjustment portion 334r comprises an extended focus range demand mode portion 337 and an accurate image demand mode portion 338. The extended focus range demand mode portion 337 is responsive to the generation and/or input of an extended focus range demand signal (e.g., over the signal and control bus 395), to configure the lens controller 334 to operate in an extended focus range mode, wherein the VFL lens 370 is operated at a first operating resonant frequency that provides a periodically modulated first optical power variation having a relatively larger amplitude, to thereby provide a first relatively larger focus range for the imaging system 300. The accurate image demand mode portion 338 is responsive to the generation and/or input of an accurate image demand signal (e.g., over the signal and control bus 395), to configure the lens controller 334 to operate in an accurate imaging mode, wherein the VFL lens 370 is operated at a second operating resonant frequency that provides a periodically modulated second optical power variation having a relatively smaller amplitude. It thereby provides a second relatively smaller focus range for the imaging system 300, but more importantly the second operating frequency is also selected to operate the VFL lens to provide low aberration images that are suitable for precision metrology inspection operations, as described in greater detail below.

As shown in FIG. 3, using the first optical power variation, the focus position FP of the imaging system 300 may be moved within an autofocus search range $R_{src}$ bound by a focus position FP1' and a focus position FP2'. Using the second optical power variation, the focus position FP may be moved within an accurate imaging focus range $R_{acc}$ bound by a focus position FP1 and a focus position FP2. It should be appreciated that the imaging system may be configured such that when the VFL lens operates at the second operating resonant frequency to provide the second optical power variation, it thereby provides the second relatively smaller focus range and also provides low aberration images that are suitable for precision metrology inspection operations. In various implementations, this may be characterized as operating the VFL lens in a "normal" imaging mode, wherein the VFL is operated to provide desirable optical characteristics (e.g., in terms of clear aperture, low aberrations, etc.) that are furthermore well matched to the other optical components in the imaging system, according to known optical design principles. In contrast, the imaging system may be configured such that when the VFL lens is operated at the first operating resonant frequency to provide the first optical power variation, the primary or only purpose is to thereby provide the first relatively larger focus range (e.g., to enable a large autofocus search range.) In various implementations, this may be characterized as operating the VFL lens in an abnormal imaging mode, wherein the emphasis on obtaining a larger optical power variation and focus range requires the acceptance of certain undesirable optical characteristics (e.g., in terms of clear aperture size, low aberrations, etc.) that are furthermore poorly matched to the other optical components in the imaging system. (Such frequency dependent optical characteristics are described in greater detail below with reference to FIG. 4.) As a result, in this mode, the imaging system may only provide relatively aberrated images (e.g., quite blurry and distorted images, in some embodiments) that are usable for performing the autofocus search operations outlined herein, but that are not suited for precision metrology inspection operations (and in some cases not even suited for user observation). It should be appreciated that an image stack in which the best workpiece image (e.g., wherein the workpiece is at the best focus position of the imaging system) is obtained through a consistently blurry or aberrated imaging system may still be used to construct a contrast curve having a peak that identifies a workpiece location or distance according to known methods, provided only that the best workpiece image is less blurred (better contrast) than other images in the image stack. Similarly, the best photodetector signal from an optical focus monitoring configuration may be obtained through a consistently blurry or aberrated imaging system when a workpiece is at the best focus position, and may still be used to identify a workpiece location or distance according to known methods, provided only that the best photodetector signal is better than photodetector signals obtained when the workpiece is located away from the best focus position.

In general, with respect to the example of FIG. 3, it will be appreciated that certain of the illustrated dimensions may not be to scale. For example, the VFL lens 370 may have different proportional dimensions than those illustrated (e.g., may be less wide and up to 50 mm long or longer for certain applications in order to provide a desired amount of lensing power, etc.).

Figure 4:
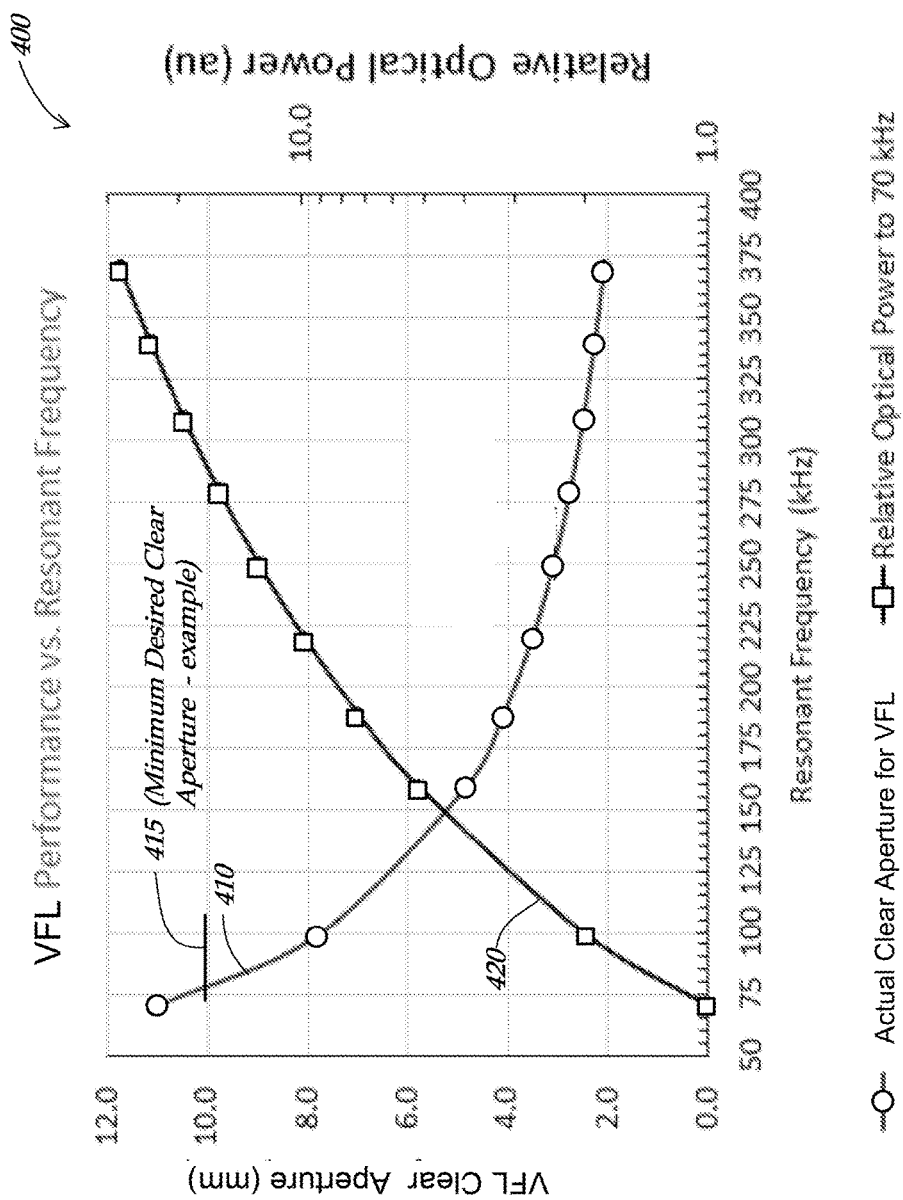
FIG. 4 is a diagram of a graph illustrating lens performance versus resonant frequency for one type of variable focal length lens.

FIG. 4 is a diagram of a graph 400 illustrating one exemplary set of VFL lens optical characteristics versus resonant operating frequency. In this particular example the VFL lens is a commercially available TAG lens. A line 410 represents the clear aperture for a VFL TAG lens plotted versus its resonant operating frequency. For a TAG lens, the clear aperture may approximately correspond to a diameter inside the first ring of a Bessel function characterizing the TAG lens refraction profile at any particular operating frequency. For the line 410, the frequency is indicated in terms of kHz on the x-axis, and the clear aperture is measured in millimeters which is indicated on the y-axis (in accordance with the scale on the left side of the graph 400). The line 410 illustrates how the clear aperture decreases as the resonant frequency increases. More specifically, the actual effective aperture is shown to drop over a range starting at approximately 11 mm for the operating frequency of 70 kHz, to approximately 2 mm at the operating frequency of approximately 370 kHz. In various implementations, a minimum desired clear aperture level 415 may be established, below which the image quality may be determined to be negatively affected. For example, in accordance with the example of FIG. 4, for minimum desired clear aperture level 415 of approximately 10 mm, the maximum associated operating frequency is on the order of 70 kHz. For minimum desired clear aperture level of approximately 6 mm, the maximum associated operating frequency is on the order of 125 kHz.

Regarding the clear aperture, it should be appreciated that elements of an optical system (e.g., the optical system 300 shown in FIG. 3) outside the VFL lens (e.g., the TAG lens) may define the limiting aperture of the imaging system. For accurate, diffraction limited, low aberration images, the clear aperture in the VFL (TAG) lens should be as large as the limiting aperture defined by the remainder of the imaging system as projected to the location of the VFL (TAG) lens clear aperture. Based on the foregoing, in some implementations, the VFL lens may be a TAG lens. The first operating resonant frequency may be a relatively lower frequency and the second operating resonant frequency may be a relatively higher frequency. In one example, in some implementations, at least a 6 millimeter clear aperture may be desired and the first operating resonant frequency may be less than 125 KHz and the second operating resonant frequency may be greater than 125 KHz.

As further illustrated in FIG. 4, a second line 420 represents a relative maximum optical power for the VFL TAG lens as plotted versus its resonant operating frequency. For the line 420, the frequency is indicated in terms of kHz on the x-axis, and the relative optical power is measured in terms of multiples of the optical power at 70 kHz which is indicated on the y-axis (in accordance with the scale on the right side of the graph 400). It will be appreciated that the lines 410 and 420 are thus plotted with respect to different types of units on the y-axis (e.g., millimeters vs. multiples of optical power), and are only provided on the same graph for purposes of illustrating the various optical characteristics that occur simultaneously as the frequency is increased. With respect to the line 420, the relative optical power is shown to increase as the frequency increases. More specifically, the relative optical power is shown to increase over a range starting at a value of 1 at the operating frequency of 70 kHz, to a value of approximately 25 at the operating frequency of approximately 370 kHz.

In one specific exemplary embodiment using a known TAG lens, when the imaging system comprises low NA objective lenses and optics (e.g., for low magnification), a second operating resonant frequency of 70 kHz may be required in the TAG lens in order to provide a large clear aperture (e.g., at least 10 millimeters, as shown in FIG. 4) in the TAG lens to provide diffraction limited images. In contrast, in order to provide a large optical power variation (large focus range) a first operating resonant frequency of 189 kHz may be used in the TAG lens (e.g., to provide a relative optical power of approximately 8, or about 8 times the focus range provide at 70 kHz). As indicated by the line (curve) 410, this will provide a much smaller first ring of a Bessel function characterizing the TAG lens refraction profile at this frequency, and in fact may position one or more additional Bessel rings (e.g., the second Bessel ring) within the limiting aperture defined by the remainder of the imaging system (e.g., assuming the remainder of the imaging system remains fixed). As such, the resulting images through the TAG lens may have significant aberration (e.g., they may appear quite blurry). However, they may still be utilized for determining the nominal position of, or distance to, a workpiece according to principles disclosed herein. It may be appreciated that the modulated focus characteristics associated with the focus of the second Bessel ring (which approximates an annular lens) will not generally match those of the first Bessel ring. In particular the optical power associated with the second Bessel ring may be significantly less than that associated with the first Bessel ring. In some implementations, this may introduce signal contamination or noise into the desired focus signal associated with the first Bessel ring. Accordingly, in some embodiments, low pass and/or high pass spatial frequency filtering may be performed (e.g., according to known methods such as Fourier analysis and/or filtering in the Fourier domain) on image data associated with the first operating resonant frequency, in order to suppress focus signal contributions associated with the second Bessel ring. Effective spatial filtering and/or signal processing parameters may be based on the differing optical characteristics associated with first and or second Bessel rings (e.g., the associated numerical apertures, etc.), and the effectiveness of spatial filtering parameters may be determined by analysis or experiment, according to known methods.

For this specific example, in one embodiment of the imaging system 300, the first operating resonant frequency of 189 kHz may provide a first relatively larger focus range of approximately 8.0 mm. The second operating resonant frequency of 70 kHz may provide a second relatively smaller focus range of approximately 0.64 mm.

Figure 5:
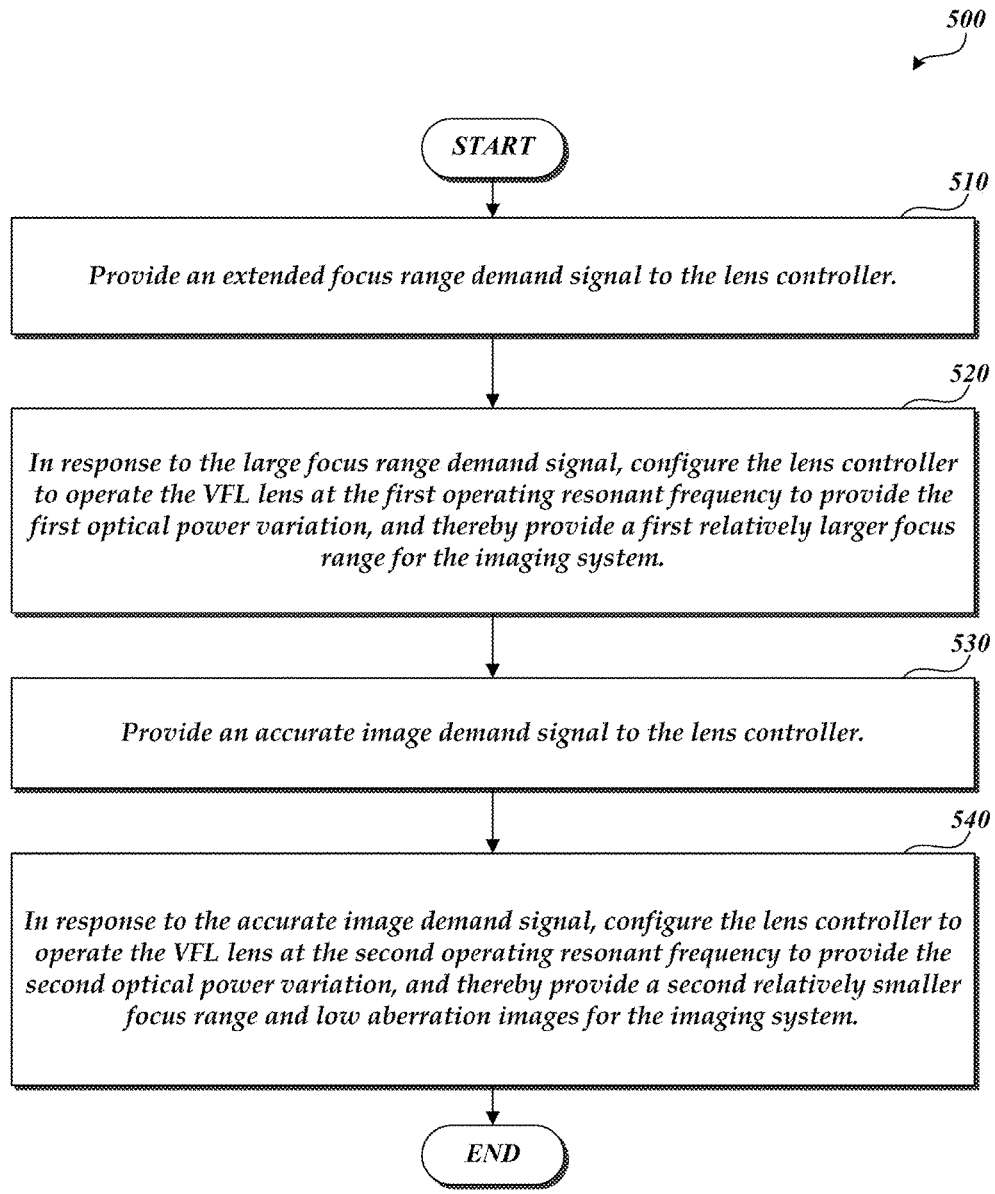
FIG. 5 is a flow diagram illustrating one exemplary implementation of a routine for operating an imaging system including a variable focal length lens.

FIG. 5 is a flow diagram illustrating one exemplary implementation of a routine 500 for operating an imaging system comprising a VFL lens, a lens controller, and a camera configured to provide images for the imaging system. In various embodiments, the VFL lens may be a high speed VFL lens having a first operating resonant frequency that provides a periodically modulated first optical power variation having a relatively larger amplitude, and having a second operating resonant frequency that provides a periodically modulated second optical power variation having a relatively smaller amplitude and that provides relatively low aberration in the imaging system. For example, a VFL TAG lens may provide such operating characteristics, as previously outlined.

At a block 510, an extended focus range demand signal is provided to the lens controller.

At a block 520, in response to the extended focus range demand signal, the lens controller is configured to operate the VFL lens at the first operating resonant frequency to provide the first optical power variation, and thereby provide a first relatively larger focus range for the imaging system.

At a block 530, an accurate image demand signal is provided to the lens controller.

At a block 540, in response to the accurate image demand signal, the lens controller is configured to operate the VFL lens at the second operating resonant frequency to provide the second optical power variation, and thereby provide a second relatively smaller focus range and low aberration images for the imaging system.

In some implementations, the accurate image demand signal may be automatically provided in the lens controller when the extended focus range demand signal is not being provided to the lens controller. In some implementations, the provided extended focus range demand signal may have an effective duration that automatically expires in the lens controller, and the accurate image demand signal may be automatically provided in the lens controller following the expiration of the effective duration.

It will be appreciated that the routine 500 includes operations usable to provide a low aberration imaging mode that is usable to acquire desirable inspection images over a relatively smaller focus range, and operations usable to provide an extended focus range mode that is suitable for performing autofocus search operations to determine a location or height of the workpiece feature over a relatively large search range (e.g., several millimeters). The autofocus search operations may be performed at a high rate (e.g., in much less than 1 second), and without mechanically reconfiguring imaging system or requiring relative motion between imaging system and workpiece feature in order to provide the relatively large search range. An autofocus search operation need not necessarily actively or automatically adjust an imaging system or a workpiece feature to provide a focused image (although it may do so, in some implementations). In some cases an autofocus search operation may simply identify the current location of, or distance to, a workpiece feature, without performing any adjustment.

That is, in some implementations, an autofocus search may be performed in conjunction with a system including the routine 500 by positioning a workpiece feature within a field of view (FOV) of the imaging system and operating the imaging system to perform autofocus search operations to determine a location or height of the workpiece feature. The autofocus search operations may comprise: S1) providing the extended focus range demand signal to the lens controller, S2) in response to the extended focus range demand signal, configuring the lens controller to periodically modulate the VFL lens at the first operating resonant frequency and periodically modulate the focus of the imaging system over the first focus range, S3) analyzing a focus signal acquired while periodically modulating the focus of the imaging system over the first focus range, and S4) determining the location or height of the workpiece feature based on the focus signal. In some implementations the focus signal may comprise analyzing a contrast metric based on an image stack acquired while periodically modulating the focus of the imaging system over the first focus range (e.g., as previously outlined with reference to the optical focus signal processing portion 375 in FIG. 3). In some implementations the focus signal may comprise a signal from a photodetector included in an optical focus monitoring configuration (e.g., as previously outlined with reference to the element 376 in FIG. 3).

In some implementations, based on the determined location or height of the workpiece feature (e.g., as outlined above), the distance between the workpiece feature and the imaging system may be manually or automatically adjusted such that the workpiece feature is located within the second relatively smaller focus range associated with the second operating resonant frequency. In such a case, observation or inspection of the workpiece feature may then take advantage of operations comprising: Ai1) providing the accurate image demand signal to the lens controller, Ai2) in response to the accurate image demand signal, Ai3) configuring the lens controller to periodically modulate the VFL lens at the second operating resonant frequency and periodically modulate the focus of the imaging system over the second focus range, and Ai4) operating the imaging system to provide a low aberration image of the workpiece feature while periodically modulating the focus of the imaging system over the second focus range.

In some implementations, the imaging system may be operated in a mode wherein operating the imaging system to perform autofocus search operations to determine a location or height of the workpiece feature (e.g., as outlined above in steps S1-S4) is automatically repeated at a predetermined rate. It will be appreciated that the autofocus search outlined above may be performed in a very short amount of time (e.g., much less than a second, in some embodiments), and may therefore be performed as an intermittent background operation without disturbing the user, in some embodiments. In some implementations, when location or height of the workpiece feature is determined to be within the second focus range by an autofocus search operation, then the observation and/or imaging operations Ai1)-Ai4), outlined above, may be automatically performed. In some implementations, when the location or height of the workpiece feature is determined to not be within the second focus range by an autofocus search operation, then the distance between the workpiece feature and the imaging system may be manually, semi-automatically, or automatically adjusted (e.g., by a motion control system associated with the imaging system) based on the determined location or height of the workpiece feature, such that the workpiece feature is located within the second relatively smaller focus range.

In various implementations, the extended focus range demand signal may be provided as a result of a user input corresponding to an extended range workpiece search or extended range autofocus operation in a user interface associated with the imaging system. In some implementations, the imaging system may be incorporated in a machine vision inspection system which includes the user interface.

As previously disclosed, in some implementations, the imaging system may be incorporated in a programmable machine vision inspection system. In such implementations the extended focus range demand signal and the accurate image demand signal may be the result of programmable instructions executed on the programmable machine vision inspection system. As indicated above, when the VFL lens is operated at the first operating resonant frequency to provide the first relatively larger focus range, this may provide blurry images that are usable for performing the autofocus search operations outlined herein, but that are not suited for precision metrology inspection operations. Therefore, in some such implementations, the programmable machine vision inspection system and/or its associated program generation and execution system may be configured such that programmable instructions associated with acquiring an image used for performing inspection operations (e.g., as implemented using a video tool) may only be executed when the accurate image demand signal is operative.

In one example of operations, an imaging system may be operated to switch from the second operating resonant frequency to the first operating resonant frequency, and provide stable operation in approximately 1 second or less, in various imaging systems. An autofocus search based on an image stack may be performed using a 60 Hz camera which captures 37 images using strobe illumination over a first relatively larger focus range of 8.0 mm in order to provide stack steps of 215 μm. An autofocus metric may be used to define a contrast curve to determine a best focus position (workpiece position) corresponding to the curve peak, in approximately 600 ms. The workpiece position relative to the imaging system may be adjusted such that the best focus position coincides with the second focus range. The imaging system may be switched from the first operating resonant frequency to the second operating resonant frequency in order to provide accurate inspection images of the workpiece within the second focus range.

Although various principles disclosed herein are particularly advantageous when used in implementations wherein the VFL lens is a TAG lens, the principles may be employed in some implementations wherein the VFL lens comprises another type of lens. As one additional example, a fluid filled membrane lens or other type of VFL lens may be advantageously operated at various resonant frequencies to provide a periodic focus modulation in an imaging system. In such an implementation, the first operating resonant frequency that provides the large focus range may be lower than the second operating frequency, in that in many mechanical systems lower frequencies may be associated with larger deformation amplitudes at resonance (e.g., as used to provide larger lens curvature). In addition, the driving signal used to provide the periodic focus modulation for the first operating resonant frequency may be larger than that used for the second operating resonant frequency in order to provide the desired large focus range. The deformation (lens curvature) at the second operating resonant frequency may therefore be less, which may provide a more ideal membrane curvature for lower aberration and better images.

While preferred implementations of the present disclosure have been illustrated and described, numerous variations in the illustrated and described arrangements of features and sequences of operations will be apparent to one skilled in the art based on this disclosure. Various alternative forms may be used to implement the principles disclosed herein. In addition, the various implementations described above can be combined to provide further implementations. All of the U.S. patents and U.S. patent applications referred to in this specification are incorporated herein by reference, in their entirety. Aspects of the implementations can be modified, if necessary to employ concepts of the various patents and applications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled.

The invention claimed is:

1. A method for controlling an imaging system comprising: a high speed variable focal length (VFL) lens having a first operating resonant frequency that provides a periodically modulated first optical power variation having a relatively larger amplitude, and having a second operating resonant frequency that provides a periodically modulated second optical power variation having a relatively smaller amplitude and that provides relatively low aberration in the imaging system; a lens controller; and a camera configured to provide images for the imaging system, the method comprising:
   providing an extended focus range demand signal to the lens controller;
   in response to the extended focus range demand signal, configuring the lens controller to operate the VFL lens at the first operating resonant frequency to provide the first optical power variation, and thereby provide a first relatively larger focus range for the imaging system;
   providing an accurate image demand signal to the lens controller; and
   in response to the accurate image demand signal, configuring the lens controller to operate the VFL lens at the second operating resonant frequency to provide the second optical power variation, and thereby provide a second relatively smaller focus range and low aberration images for the imaging system.

2. The method of claim 1, further comprising:
positioning a workpiece feature within a field of view (FOV) of the imaging system; and
operating the imaging system to perform autofocus search operations to determine a location or height of the workpiece feature, comprising:
   providing the extended focus range demand signal to the lens controller;
   in response to the extended focus range demand signal, configuring the lens controller to periodically modulate the VFL lens at the first operating resonant frequency and periodically modulate a focus of the imaging system over the first relatively larger focus range;
   analyzing a focus signal acquired while periodically modulating the focus of the imaging system over the first relatively larger focus range; and
   determining the location or height of the workpiece feature based on the focus signal.

3. The method of claim 2, further comprising:
adjusting a distance between the workpiece feature and the imaging system based on the determined location or height of the workpiece feature, such that the workpiece feature is located within the second relatively smaller focus range.

4. The method of claim 3, further comprising:
providing the accurate image demand signal to the lens controller;
in response to the accurate image demand signal, configuring the lens controller to periodically modulate the VFL lens at the second operating resonant frequency and periodically modulate the focus of the imaging system over the second relatively smaller focus range; and
operating the imaging system to provide a low aberration image of the workpiece feature while periodically modulating the focus of the imaging system over the second relatively smaller focus range.

5. The method of claim 2, further comprising operating the imaging system in a mode wherein the step of operating the imaging system to perform autofocus search operations to determine a location or height of the workpiece feature is automatically repeated at a predetermined rate.

6. The method of claim 5, wherein when the determined location or height of the workpiece feature is within the second relatively smaller focus range, then the method further comprises automatic operations including:
provide the accurate image demand signal to the lens controller;
in response to the accurate image demand signal, configuring the lens controller to periodically modulate the VFL lens at the second operating resonant frequency and periodically modulate the focus of the imaging system over the second relatively smaller focus range; and
operating the imaging system to provide a low aberration image of the workpiece feature while periodically modulating the focus of the imaging system over the second relatively smaller focus range.

7. The method of claim 5, wherein when the determined location or height of the workpiece feature is not within the second relatively smaller focus range, then the method further comprises operations including:
adjusting a distance between the workpiece feature and the imaging system based on the determined location or height of the workpiece feature, such that the workpiece feature is located within the second relatively smaller focus range.

8. The method of claim 2, wherein analyzing the focus signal comprises analyzing a contrast metric based on an image stack acquired while periodically modulating the focus of the imaging system over the first relatively larger focus range.

9. The method of claim 2, wherein the focus signal comprises a signal from a photodetector included in an optical focus monitoring configuration.

10. The method of claim 1, wherein the extended focus range demand signal is provided as a result of a user input corresponding to an extended range workpiece search or extended range autofocus operation in a user interface associated with the imaging system.

11. The method of claim 10, wherein the imaging system is incorporated in a machine vision inspection system which includes the user interface.

12. The method of claim 1, wherein the imaging system is incorporated in a programmable machine vision inspection system, and the extended focus range demand signal and the accurate image demand signal are the result of programmable instructions executed on the programmable machine vision inspection system.

13. The method of claim 1, wherein the imaging system is configured such that:
operating the VFL lens at the second operating resonant frequency provides the second optical power variation, and thereby provides the second relatively smaller focus range and low aberration images that are suitable for precision metrology inspection operations; and
operating the VFL lens at the first operating resonant frequency provides the first optical power variation, and thereby provides the first relatively larger focus range but also provides relatively aberrated images that are usable for performing autofocus search operations, but that are not suited for precision metrology inspection operations.

14. The method of claim 13, wherein the imaging system is incorporated in a programmable machine vision inspection system, and the extended focus range demand signal and the accurate image demand signal are the result of programmable instructions executed on the programmable machine vision inspection system, and programmable instructions associated with acquiring an image used for performing precision metrology inspection operations are only executed when the accurate image demand signal is operative.

15. The method of claim 1, wherein the VFL lens is a VFL tunable acoustic gradient (TAG) lens, and the first operating resonant frequency is a relatively lower frequency and the second operating resonant frequency is a relatively higher frequency.

16. The method of claim 15, wherein the first operating resonant frequency is less than 125 KHz and the second operating resonant frequency is greater than 125 KHz.

17. The method of claim 1, wherein the accurate image demand signal is automatically provided in the lens controller when the extended focus range demand signal is not being provided to the lens controller.

18. The method of claim 17, wherein the extended focus range demand signal has an effective duration that automatically expires in the lens controller, and the accurate image demand signal is automatically provided in the lens controller following the expiration of the effective duration.

* * * * *